United States Patent
Aldrich

Patent Number: 6,064,898
Date of Patent: May 16, 2000

[54] NON-INVASIVE BLOOD COMPONENT ANALYZER

[75] Inventor: Thomas K Aldrich, Pelham, N.Y.

[73] Assignee: Essential Medical Devices, Pelham, N.Y.

[21] Appl. No.: 09/157,453

[22] Filed: Sep. 21, 1998

[51] Int. Cl.[7] ........................................ A61B 5/00
[52] U.S. Cl. .................... 600/316; 600/322; 600/323; 600/328
[58] Field of Search ....................... 600/310, 315, 600/316, 319, 322, 323, 326, 328, 330, 335, 336, 407, 473, 476

[56] References Cited

U.S. PATENT DOCUMENTS

| | | |
|---|---|---|
| 3,958,560 | 5/1976 | March . |
| 4,167,331 | 9/1979 | Nielsen . |
| 4,194,217 | 3/1980 | van den Bosch . |
| 4,394,572 | 7/1983 | Wilber . |
| 4,407,290 | 10/1983 | Wilber . |
| 4,621,643 | 11/1986 | New et al. . |
| 4,653,498 | 3/1987 | New et al. . |
| 4,655,225 | 4/1987 | Dahn et al. . |
| 4,700,708 | 10/1987 | New et al. . |
| 4,714,080 | 12/1987 | Edgar et al. . |
| 4,770,179 | 9/1988 | New et al. . |
| 4,819,752 | 4/1989 | Zelin . |
| 4,882,492 | 11/1989 | Schlager . |
| 4,909,259 | 3/1990 | Tehrani . |
| 4,934,372 | 6/1990 | Corenmn et al. . |
| 4,997,769 | 3/1991 | Lundsgard . |
| 5,009,230 | 4/1991 | Hutchinson . |
| 5,028,787 | 7/1991 | Rosenthal et al. . |
| 5,086,229 | 2/1992 | Rosenthal et al. . |
| 5,101,825 | 4/1992 | Gravenstein, et al. . |
| 5,137,023 | 8/1992 | Mendelson et al. . |
| 5,139,025 | 8/1992 | Lewis et al. ........................ 600/477 |
| 5,184,672 | 2/1993 | Chance et al. ........................ 600/407 |
| 5,285,782 | 2/1994 | Prosser . |
| 5,297,548 | 3/1994 | Pologe . |
| 5,313,941 | 5/1994 | Braig et al. . |

(List continued on next page.)

FOREIGN PATENT DOCUMENTS

| | | |
|---|---|---|
| 0536304 | 6/1986 | European Pat. Off. . |
| 0208201 | 12/1996 | European Pat. Off. . |
| 0374190 | 1/1997 | European Pat. Off. . |
| 4238641 | 5/1994 | Germany . |
| 888931 | 12/1981 | Russian Federation . |

OTHER PUBLICATIONS

Arnold MA. Noninvasive blood glucose monitoring. *Curr Opinion Biotech* 7:46–9, 1996.

Cavinato AG, Mayes DM, Ge ZH, Callis JB. Noninvasive method for monitoring ethanol in fermentation process using fiberoptic near–infrared spectroscopy. *Anal Chem* 62:1977–82, 1990.

Hall JW, Pollard A. Near–infrared spectroscopic determination of serum total proteins, albumin, globulins, and urea. *Clin Biochem* 26:483–90, 1993.

Hall et al., Near Infrared Spectrophotometry: A New Dimension in Clinical Chemistry. *Clin. Chem* 38/9, 1623–31 (1992).

Hanning CD, Alexander–Williams JM. Pulse Oximetry: a practical review. *BMJ* 311:367–70, 1995.

Heise HM, Marbach R, Koschinsky T, Gries FA. Noninvasive blood glucose sensors base on near infrared spectroscopy. *Artif Organs* 18:439–47, 1994.

(List continued on next page.)

*Primary Examiner*—Eric F. Winakur
*Attorney, Agent, or Firm*—Patterson, Belknap, Webb & Tyler, LLP

[57] ABSTRACT

A non-invasive blood component analyzer using spectrophotometry, with systole/diastole corrections for tissue absorbance, and with built-in monitoring of light path length to allow its accurate use in subjects with widely varying finger size and/or varying pulse amplitude. Blood components that are able to be analyzed include oxyhemoglobin, total hemoglobin, bilirubin, glucose, hormone levels and a variety of drugs.

50 Claims, 5 Drawing Sheets

U.S. PATENT DOCUMENTS

| | | |
|---|---|---|
| 5,355,880 | 10/1994 | Thomas et al. . |
| 5,360,004 | 11/1994 | Purdy et al. . |
| 5,372,136 | 12/1994 | Steuer, et al. . |
| 5,413,100 | 5/1995 | Barthelemy et al. . |
| 5,435,309 | 7/1995 | Thomas et al. . |
| 5,490,505 | 2/1996 | Diab et al. . |
| 5,491,341 | 2/1996 | McCaul et al. . |
| 5,503,148 | 4/1996 | Pologe et al. ............................ 600/323 |
| 5,522,388 | 6/1996 | Ishikawa, et al. . |
| 5,553,615 | 9/1996 | Carim et al. . |
| 5,636,633 | 6/1997 | Messerschmidt, et al. . |
| 5,638,816 | 6/1997 | Kiani-Azarbayjaney et al. . |
| 5,655,530 | 8/1997 | Messerschmidt, et al. . |
| 5,722,398 | 3/1998 | Ishihara, et al. . |
| 5,741,213 | 4/1998 | Kouchi, et al. . |
| 5,769,076 | 6/1998 | Maekawa, et al. . |
| 5,823,951 | 10/1998 | Messerschmidt, et al. . |
| 5,842,979 | 12/1998 | Jarman ..................................... 600/322 |
| 5,869,971 | 2/1999 | Sherman . |

OTHER PUBLICATIONS

Mancini E, Santoro A, Sporgano M, Paolini F, Rossi M. Zucchelli P. Continuous on–line optical absorbance recording of blood volume changes during hemodialysis. *Artif Organs* 17:691–4, 1993.

Linder et al. Noninvasive Determination of Neonatal Hyperbilirubinemia: Standardization for Variation in Skin Color. *Am J Perinatology* 11:223–5, 1994.

Lindberg et al. Pulse Oximetry—Clinical implications and recent technical developments. *Acta Anaesthesiologica Scandinvavica.* 39 (1995).

Mahoney et al. Measurement of Caraboxyhemoglobin and Total Hemoglobin by Five Specialized Spectrophotometers (Co–oximeters) in Comparison with Reference Methods. *Clin Chem* 39/8, 1693–1700 (1993).

McDonald OL, Watts MT. Use of commercially prepared control sera as quality control materials for spectrophotometric bilirubin determinations in amniotic fluid. *Am J Clin Pathol* 84:51307, 1985.

Mendelson Y. Pulse oximetry: theory and applications for noninvasive monitoring. *Clinical Chemistry* 38:1601–7, 1992.

Pickup, J. Developing Glucose Sensors for in vivo use. *Trends in Biotech.* 1993 11:285–91.

Robinson MR, Eaton RP, Haaland DM, Koepp GW, Thomas EV, Stallard BR, Robinson PL. Noninvasive glucose monitoring in diabetic patients: a preliminary evaluation. *Clin Chem* 38:1618–22, 1992.

Ruchala PL, Siebold L. Stremsterfer K. Validating assessment of neonatal jaundice with transcutaneous bilirubin measurement. *Neonatal Network* 15:33–7, 1996.

Sanchez–Carillo Cl, Ramirez–Sanchez T de J, Zambrana–Castaneda M, Selwyn BJ. Test of a noninvasive instrument for measuring hemoglobin concentration. *Intl J Technology* 5:659–67, 1989.

Severinghaus JS and Kelleher JF. Recent developments in pulse oximetry, *Anesthesiology* 76:1018–38, 1992.

Siek TJ, Rieders F. Determination of carboxyhemoglobin in the presence of other blood hemoglobin pigments by visible spectrophotometry. *J Forensic Sci* 29:39–54, 1984.

Vegfers et al. Carbosyhaemoglobinaemia and pulse oximetry. *Brit J Anaesth* 66:625–6, 1991.

Yamamoto Y, Oberg PA. Measurement of digital blood flow using the laser Doppler, impedance, and strain gauge methods. *Med Biol Eng Comput* 28:113–8, 1990.

Zeller H, Novak P, Landgraf R. Blood Glucose measurement by infrared spectroscopy. *Intl J. Artif Org* 12:12–35, 1989.

Zijistra et al. Performance of an Automated Six–Wavelength Photometr (Radiometer 0SM3) for Routine Measurement of Hemoglobin Donvestives. *Clin Chem* 34/1 149152 (1988).

Merschbrock U., et al., Fast wavelength scanning reflectance spectrophotometer for noninvasive determination of hemoglobin oxygenation in human skin. *Int J Microcirc Clin Exp* 1994 Sept.–Oct.; 14(5):274–81.

Rao, V.M., et al., Noninvasive diagnostic imaging in hemoglobinopathies. *Hematol Oncol Clin North Am* 1991 June; 5(3):517–33.

Takatani S, Eheung P.W., Ernst E.A., A noninvasive tissue reflectance oximeter. An instrument for measurement of tissue hemoglobin oxygen saturation in vivo. *Ann Biomed Eng* 1980; 8(1):1–15.

Yamakoshi K., Tanaka S., Shimazu H., Electrical admittance cuff for noninvasive and simultaneous measurement of haematocrit, arterial pressure and elasticity using vol.–oscillometric method. *Med Biol Eng Comput* 1994 Jul; 32(4 Suppl):S99–107.

Gravenstein, D., S. Lampotang, et al. (1994). Noninvasive hemoglobinometry. *Anethesiology* 81 (3A): A576. (Poster).

D. Li, Y. Wang, D. Waight., Blood oxygen saturation assessment in vivo using $T2^*$ estimation, *MRM* 1998, 39:685–690.

Steuer, R. R., D. H. Harris et al. (1991). Evaluationof a noninvasive hematocrit monitor: a new technology. *Am Clin Lab* 10(6): 20–2.

Yamakoshi, K. I., H. Shimazu, et al. (1980). Noninvasive measurement of hematocrit by electrical admittance plethysmography techniue. IEEE *Trans Blomed Eng* 27(3): 154–61.

NON-INVASIVE BLOOD COMPONENT ANALYZER

BACKGROUND OF THE INVENTION

1. Field of the Invention

The present invention is directed to a non-invasive device and method for analyzing the concentration of blood components, including oxygen saturation, bilirubin, hemoglobin, glucose, hormones and a variety of drugs.

2. Description of the Prior Art

Analysis of blood components is regularly required in hospitals, emergency rooms, doctors' offices, and in patients' homes (in the case of blood glucose analysis for example), for a variety of diagnostic purposes and to monitor therapy. In most cases, blood is obtained by venipuncture or finger prick, which raises small but important concerns regarding pain and the potential for transmission of infectious disease, such as viral hepatitis and human immunodeficiency virus (HIV) infection. The pain associated with blood drawing often inhibits patient compliance with prescribed blood testing, leading to potentially dangerous consequences of undiagnosed disease. Also, the need for trained technicians to draw and handle blood contributes to the high cost of medical care. Furthermore, blood testing procedures take time, which often delays diagnosis. Finally, for practical reasons, blood testing can be done only at intervals, providing only "snap-snot" data regarding the blood component of interest. Under some circumstances, as for example during the assessment of blood losses due to gastrointestinal hemorrhage or during the assessment of the response to hemodialysis, to the treatment of diabetic ketoacidosis, or to the treatment of acute intoxications, it would be desirable to monitor the concentration of one or more blood components continuously.

Blood tests are often performed in "panels;" that is, a number of tests is run on a single drawn blood sample. However, there are also clinical circumstances in which only a single or a small number of tests are required, or when a single test must be performed repeatedly over time. In such cases, noninvasive tests that do not require blood drawing would be particularly useful.

An example of a currently available noninvasive test is pulse oximetry, which measures the adequacy of saturation of arterial blood hemoglobin with oxygen. Mendelson Y., *Pulse Oximetry: Theory and Applications for Noninvasive Monitoring, Clinical Chemistry* 38: 1601–7, 1992; Hanning CD, Alexander-Williams J M., *Pulse Oximetry: A Practical Review, BMJ* 311:367–70, 1995; Severinghaus J W and Kelleher J F., *Recent developments in pulse oximetry, Anesthesiology* 76:1018–38, 1992; Corenman et al., U.S. Pat. No. 4,934,372; Edgar et al., U.S. Pat. No. 4,714,080; Zelin, U.S. Pat. No. 4,819,752; and Wilber, U.S. Pat. No. 4,407,290. Oximeters have become indispensable for screening patients for life-threatening hypoxemia and for monitoring patient safety during procedures such as surgery and childbirth. Oximeters reliably report the relative arterial oxygen level (percent of the maximum that can be carried by the available hemoglobin), but they cannot measure absolute oxygen content of the blood, because their readings are independent of hemoglobin concentration.

In pulse oximeters, light produced by two light-emitting diodes (LEDs) at approximately 660 nm (red) and 940 nm (infrared) are alternately passed through the subject's finger, toe, or ear (or other well-perfused tissue), and the transmitted light is measured by a rapidly-responding photodetector. The light that is not transmitted to the photodetector is absorbed by the finger or is scattered out of the range of the photodetector. The amount of absorbance depends on tissue density and the amount and character of the blood (venous and arterial) that is present in the light path. At each of the two wavelengths, the resulting time-varying measurement of light intensity for the wavelength, termed "photoplethysmography," is roughly inversely proportional to finger volume, which varies with the arterial pulse.

Changes in absorbance (A) are caused by changes in the amount of blood present in the light path, assumed to be primarily changes in the amount of arterial blood due to the arterial pulse. Because absorbance of oxy-hemoglobin differs for light at the two wavelengths, a ratio of change in absorbance of red to change in absorbance of infrared light can be used to measure oxy-hemoglobin percentage. In practice, transmittance ($T=10^{-A}$) is measured from each of the photoplethysmograms, absorbance ($A=\log 1/T$) is calculated, and the change in absorbance with the arterial pulse is calculated for each wavelength studied. The two changing absorbances are then electronically divided, and after inconsistent data points are discarded, the ratios are averaged to yield an average ratio of red/infrared absorbance change. The average ratio is then multiplied by a correction factor, which has been empirically determined for each instrument by comparison with oxy-hemoglobin levels measured by a co-oximeter in arterial blood samples in normal subjects with varying levels of oxyhemoglobin produced as a result of breathing gases with varying fractions of inspired oxygen ($FiO_2$).

Commercial pulse oximeters used to measure the amount of arterial blood oxygen saturation ($SaO_2$) are available from the following manufacturers: BCI International, Biochem International, Inc., Criticare Systems, Inc., Datascope Corp., Datex Instrumentation Corp., Gambro Engstrom A. B., Invivo Research, Inc., Kontron Instruments, Life Care International, Inc., MSA, Medical Research Laboratories, Minolta Camera Co., Ltd., Nellcor-Puritan-Bennett, Nippon Colin Co., Ltd., Nonin Medical Systems, Inc., Ohmeda, Inc., Palco Labs, PhysioControl, Respironics, Inc., Sensor Medics Corp., Siemens Medical Systems, Inc., Simed Corp. and Spectramed, Inc.

Pulse oximeters can be controlled with various software packages, including those made by EMG Scientific. Signal processing apparatus, such as that disclosed in U.S. Pat. No. 5,490,505, can be used to process the signals generated by a pulse oximeter.

Prior designs of pulse oximeters used to measure arterial oxygen saturation are well known. For example, U.S. Pat. No. 4,653,498 to New, Jr. et al. (1987) describes a display monitor for use with a pulse oximeter of the type wherein light of two different wavelengths is passed through body tissue, such as a finger, an ear or the scalp, so as to be modulated by the pulsatile component of arterial blood therein and thereby indicates oxygen saturation. Similarly, U.S. Pat. Nos. 4,621,643 (1986), 4,700,708 (1987) and 4,770,179 (1988), all to New, Jr. et al., describe disposable probes for use with pulse oximeters.

U.S. Pat. No. 5,810,723 to the same inventor as the instant application, which will issue on Sep. 22, 1998 from copending application number 08/759,582, is entitled Non-Invasive Carboxyhemoglobin Analyzer. In that patent an apparatus and method is disclosed which allows the non-invasive monitoring of a subject's carboxyhemoglobin level, thereby allowing the detection of possible carbon monoxide poisoning. The subject breathes oxygen to lower his reduced hemoglobin level to approximately 0%, thus allowing the detection and differentiation between oxy- and carboxyhemoglobin by modification of a conventional pulse oximeter.

Noninvasive monitors of bilirubin are also available, especially for following the course of neonatal jaundice. See Linder N, Regev A, Gazit G, Carplus M, Mandelberg A, Tamir I, Reichman B., Noninvasive determination of neonatal hyperbilirubinemia: standardization for variation in skin color; *Am J Perinatology* 11:223–5,1994. Usually, the absorbance by a body part of light near the peak absorption of bilirubin is monitored. Bilirubinometers are generally calibrated by comparison with measured blood bilirubin in the infant to be monitored. Without such calibration, the varying amounts of tissue and blood in the light path limits the accuracy of the measurements. Thus, at least one blood sample is required.

Examples of other blood tests that are often done alone and/or must be repeated at frequent intervals include: blood hemoglobin or hematocrit measurements for patients with known or suspected anemia, actively hemorrhaging from disease or surgery, and/or undergoing transfusion therapy; glycosylated hemoglobin levels in diabetic patients to assist in assessing adequacy of blood glucose control; blood glucose levels in patients with diabetes or suspected hypoglycemia, for diagnosis of hyper- or hypo-glycemia or for monitoring the effectiveness of insulin or oral hypoglycemic therapy; thyroid hormone levels in persons with hyper- or hypothyroidism; ethanol levels in patients suspected of ethanol intoxication; and a variety of drug and drug metabolite levels (e.g. digoxin, theophylline, dilantin, morphine, benzodiazepines, anabolic steroids) in patients undergoing therapy or suspected of being intoxicated with such drugs.

Noninvasive monitors for glucose, ethanol, and other blood components have been suggested, but have not proven to be feasible, accurate, and/or economically viable. Zeller H, Novak P, Landgraf R, *Blood Glucose Measurement By Infrared Spectroscopy, Intl J Artif Org* 12:12–35, 1989. Examples include the device described by March in U.S. Pat. No. 3,958,560, which measures glucose in the cornea of the eye by determining the rotation of reflected polarized infrared light. Although it does not require blood drawing, March's technique is cumbersome and uncomfortable for patients and rot suitable for routine monitoring.

The techniques of Hutchinson, U.S. Pat. No. 5,009,230; Dahne et al., U.S. Pat. No. 4,655,225; Mendelson et al., U.S. Pat. No. 5,137,023; Rosenthal et al., U.S. Pat. No. 5,028,787; Schlager et al., U.S. Pat. No. 4,882,492; U.S. Pat. No. 5,638,816, Kiani-Azarbayjary, et al.; and Purdy et al., U.S. Pat. No. 5,360,004 use near infrared light (<2.5 cm wavelength) to assess glucose or other blood components. All suffer from inaccuracies due to the relatively weak absorption bands of glucose in the near infrared spectrum, from overlapping absorption from water, proteins, or other blood components, and especially from varying amounts of blood and tissue in the optical path. Some improve their resolution by using pulsatile flow or displacement of blood as in Dahne et al., and Mendelson et al. to provide a subtractable background, but problems with varying and unknown blood path-length persist.

Braig et al., U.S. Pat. No. 5,313,941 describes a device employing mid-infrared light to measure glucose or ethanol, with synchronization of measurements with the cardiac cycle in order to factor out contributions from components of the finger other than arterial blood. Although the use of systole/diastole comparisons help to limit the interfering influences of tissues other than blood, the accuracy of the described instrument also suffers from its inability to take light path length into account. The instrument is calibrated by comparison with blood samples in volunteer subjects, but subjects with varying finger size and/or varying finger blood volume would yield varying results.

Kiani-Azarbayjany, et al., U.S. Pat. No. 5,638,816, describes a device that produces larger-scale oscillations in tissue blood volume than occur with arterial pulses and analyzes the variations in near infrared absorbances during such oscillations to measure glucose, various species of hemoglobin, and drug concentrations in blood. However, Kiani fails to account for or measure change in light path length. Kiani's device solves the problem of an unknown light path length by normalizing the measurement of the blood constituent of interest, e.g. glucose, (by absorbance at a specific infrared wavelength) against that of water (at another specific infrared wavelength). However, the use of induced pulsations invalidates the use of this device to measure specifically arterial constituents (e.g. oxyhemoglobin) and may well invalidate the measurements of specifically intravascular compounds (e.g. hemoglobin), because the pulsations are likely to cause variations in the light path length through other-than-vascular tissue. This is an especially severe problem when significant amounts of fatty tissue are present. Furthermore, the need to define and produce light at wavelengths that completely or nearly completely separate water from glucose may make the instrument expensive and unwieldy.

The availability of a simple, inexpensive, non-invasive monitoring device for measuring various other blood components would greatly simplify diagnosis, would lead to more rapid analysis of blood component concentrations and avoid the risk and discomfort of invasive methods of measuring such components.

A non-invasive blood component analyzer would likely find a substantial market among hospitals, hospital emergency rooms, community emergency medical services, physician's offices, fire and police departments and the like. An accurate, noninvasive glucose analyzer would find an even greater market for the daily, low-cost, home-based self-monitoring of blood glucose by diabetic patients.

SUMMARY OF THE INVENTION

In accordance with the invention, the above and other objects are met by the present non-invasive monitoring device and methods for analysis of blood components.

The invention described here is a noninvasive blood component analyzer using spectrophotometry, with systole/diastole corrections for tissue absorbance, and with built-in monitoring of light path length to allow its accurate use in subjects with widely varying finger size.

The present invention for analyzing and monitoring blood component concentrations in a patient is a device that simultaneously measures physical dimensions (e.g., linear distance) and the absorbance of visible and/or infrared light at one or more specific wavelengths across the patient's finger, toe, earlobe, or other body part at each of two or more points in the cardiac cycle, e.g., peak systole and nadir diastole. By these measurements and an analysis of differing absorbances and varying light path lengths, the concentration of a particular blood component can be measured and monitored over time.

Accordingly, it is an object of the present invention to provide a simple, inexpensive, non-invasive monitoring device for blood components.

It is another object of this invention to provide a device and method for simplifying the analysis of the concentration of blood components, including oxyhemoglobin, bilirubin, hemoglobin, glucose, hormones, and a variety of drugs, among others.

Another object of this invention is to provide a device and method for the analysis of blood components that can be used in hospitals, emergency rooms, doctors' offices and in patients' homes.

Yet another objective of the present invention is to provide a device and method for analyzing blood components that eases diagnosis and monitors therapy, and if so desired, can be performed by the patient.

Another object of the present invention is to provide a device and method for analyzing blood components that does not require the drawing of blood samples, thereby avoiding discomfort to the patient, the potential for transmission of infectious diseases, and which enhances patient compliance with blood testing.

BRIEF DESCRIPTION OF THE DRAWINGS

Preferred embodiments of the non-invasive blood component analyzer of the present invention are described in detail below with reference to the drawings wherein.

DETAILED DESCRIPTION OF PREFERRED EMBODIMENTS

As will become readily apparent to those skilled in the art, although the illustrations in the drawings and the description describe use of a novel non-invasive blood component analyzer, the various features described can be used alone or in combination with other features without departing from the scope of the invention set forth below in the claims.

Figure 1:
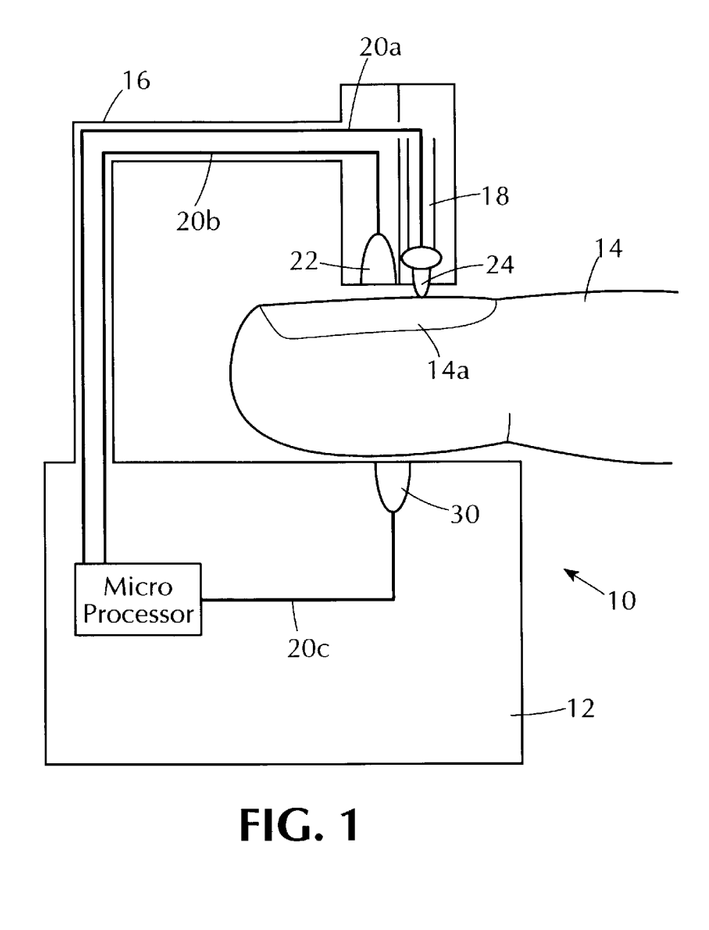
FIG. 1 is a drawing of an embodiment of the inventive non-invasive blood component analyzer.

As shown in FIG. 1, the inventive blood component analyzer 10 is made up of a base 12 which is adapted to accept the patient's finger 14 and holds the finger 14 in place by a means such as a groove, clamp or strap (not shown). The base 12 can be modified to accept and hold (or contour to) a patient's toe or ear or other well-perfused tissue, as will be recognized by one skilled in the art. Firmly embedded in base 12 is arm 16 which is adapted for holding a device for measuring one or more physical characteristics of the tissue, such as a linear displacement transducer 18 (e.g. the miniature displacement transducer made by Solartron Metrology, Buffalo, N.Y.) preferably placed against the patient's fingernail 14a or toenail. The displacement transducer 18 is connected to a microprocessor and display unit (not shown) by lead 20a. The microprocessor and display unit may be embedded in the base 12 or alternatively, the lead 20a can run to an external microprocessor and display unit. The transducer 18 must be adjustable to accommodate digits of varying sizes. This can be accomplished by various mechanical means, which will be recognized by those skilled in the art. The arm 16 is also adapted to hold one or more light-emitting diodes (LEDs), lasers, or other light sources, 22 to produce light at narrow bands of wavelengths in the visible or near-infrared range, depending on the application. The light source 22, preferably should be located as close as possible to the tip 24 of the transducer 18, in order to ensure that both the light source 22 and the transducer 18 are measuring the same tissue path. Further, the arm 16 or light source 22 should be adjustable as discussed above. The intensity of the light source 22 is controlled by the micro processor via a lead 20b. The light source 22 is positioned so as to transilluminate the subject's digit 14 or any other body part in which light absorbance of arterial blood can be detected by measuring changes in absorbance during pulsatile flow of blood. Alternatively, if the light source 22 is too bulky to be conveniently placed next to the subject's digit 14 or other tissue or too hot to be safely placed next to the tissue, it can be positioned at some distance from the tissue on one end of a fiberoptic lightguide, the other end of which is positioned next to the body part 14 alongside the transducer 18.

Light transmitted through the digit 14 is measured by one or more rapidly-responding photodetectors 30. As will be recognized by one skilled in the art, the photodetector 30 and the light source 22 can be alternatively placed in either the base 12 or the arm 16 of the analyzer 10. It is preferred to shield the photodetector 30 from ambient light. The output from the photodetector 30 is transmitted to the microprocessor via lead 20c. The photodetector 30 output is amplified, digitized at 100–500 Hz by an analog-digital converter, analyzed by a microprocessor, and stored as digital files. The microprocessor performs the necessary calculations for this information. A personal computer or some other device for computing can be substituted for the dedicated microprocessor as will be readily recognized by those skilled in the art.

When it is necessary to produce light only in the visible or very near infrared range (approximately 500–1,000 nm), as for measurements of hemoglobin or bilirubin, LEDs are the simplest, most compact, and least expensive option to serve as the light source. Alternatively, an incandescent lamp modified by filters could also be used in the visible range. In the case of near-infrared light, a modified $CO_2$ laser, emitting over a narrow band within the 9,000–10,500 nm range, while expensive, is the simplest option. An alternative is to produce a broad band of infrared emissions using a heater coil, and to narrow the emission band using etalons 152 interposed between the heater coil and the digit (or between the heater coil and one end of a lightguide, the other end of which is positioned next to the digit). Because of the risk of skin or tissue thermal injury from excessive exposure to infrared energy when infrared energy at wavelengths greater than approximately 1,200 nm are used, an electromechanical shutter 152 (e.g. Melles-Griot electronic shutter) is interposed between the light source 22 and the digit 14. The shutter is kept closed except for brief (approximately 1/60 sec) periods when photoplethysmographic measurements are required. It will be appreciated by those skilled in the art, both now and as the art progresses, that less risky or costly options can be used.

The linear distance between the light source 22 and the photodetector 30 is monitored with 0.2–0.5 μm resolution by the transducer 18. Alternatively, length is measured by a pair of opposing piezoelectric crystals (e.g. the sonomicrometer made by Triton Technologies, Inc., San Diego, Calif.), sited next to the light source(s) and the photodetector(s). One piezoelectric crystal is electrically excited to generate ultrasonic vibrations and the other piezoelectric crystal measures linear distance between the two by the duration between emission and receipt of the ultrasound signal. Because ultrasound waves do not travel well through bone, sonomicrometers are most suitable for measuring light path length in tissue that does not contain bone, e.g. earlobe, rather than fingertip. A third alternative for measuring length is by a magnetometer, consisting of a pair of coils sited next to the light source(s) and the photodetector(s); one coil generates a magnetic field and the other detects changing magnetic fields and measures linear distance between the two coils by the strength of the detected magnetic field.

The result of any of these 3 approaches to measuring the distance between the light source and the base is a "linear plethysmogram" of the fingertip or other body part. The length data are digitized at 100–500 Hz and stored along with the photodetector data. Of course, those skilled in the art will recognize that other physical characteristics, such as circumference of a digit and the changes in circumference, may also be used.

For some applications, e.g., the measurement of hemoglobin, only a single light source 22 emitting a single wavelength in the visible range will be necessary. In other cases, as for the measurement of glucose, at least two wavelengths, both in the near-infrared range, will be required. In such cases, depending on the type of light source used, interposed bandpass filters (e.g. interferometers or etalons supplied by Melles-Griol. Photonics Components, Irvine, Calif.) may be used to modify the light produced by the light source.

Figure 2:
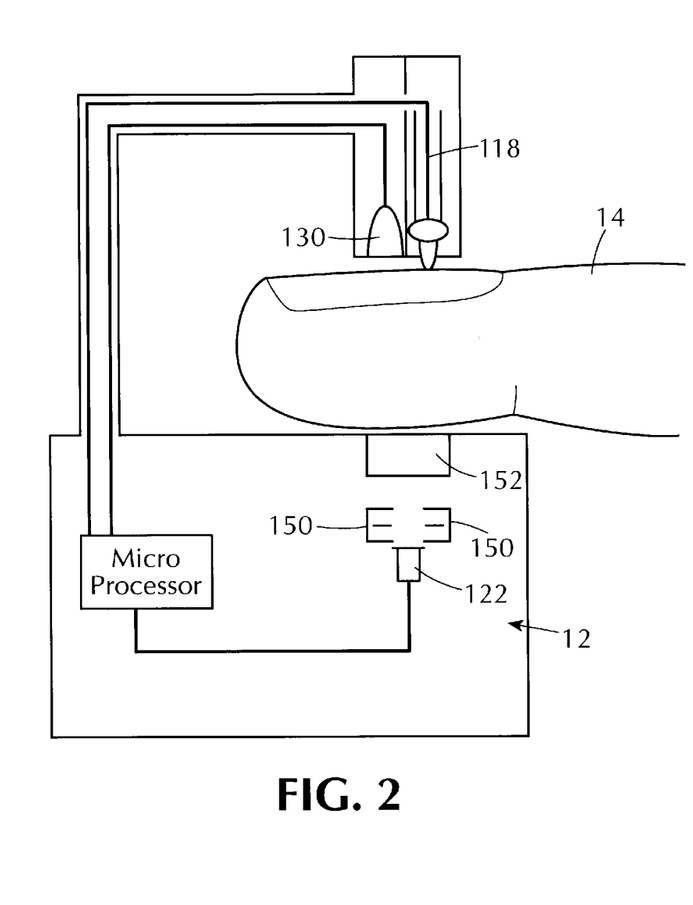
FIG. 2 is a detailed cutaway view of the detector portion of an alternative embodiment of the inventive non-invasive blood component analyzer.

Turning now to FIG. 2, an alternative embodiment is illustrated for cases in which there is no single wavelength that is strongly absorbed by the compound of interest and by no other compounds expected to be present in arterial blood, such as measuring glucose levels in the subject's blood. In FIG. 2, a single broad-band source 122 is used, and two or more bandpass filters 150 are alternately interposed between the light source and the digit 14 or other tissue, using a rotating or oscillating filter holder 152. Alternatively, two or more separate sources are used, placed adjacent to each other so that the light paths traversed by light from all of the sources to the detector are substantially identical. In this embodiment the two or more light sources are alternately switched on or with their emissions alternately blocked using electromechanical shutters (e.g., Melles-Griot electronic shutter).

When two or more different infrared wavelengths (>1200 nm) are to be investigated, appropriate bandpass filters 150 are sequentially interposed between the digit 114 and the light source 122 for brief periods of time, e.g., 10–20 msec each, by means of a rotating filter holder 152. In another embodiment, two or more light sources are used, alternately switched on for brief periods of time, e.g. 10 msec, or with their emissions alternately blocked by shutters. The photo-detector 130 output is monitored during periods of time separately identified as occurring during exposure to each wavelength. For each systole or diastole, average transmittance (T) at each of the relevant wavelengths and average light path length (e) are recorded/computed, and absorbance (A) is calculated as A=log 1/T.

In the embodiment of FIG. 2, where the analyzer 10 is specially adapted to measured substances such as glucose, which requires two or more wavelengths of infrared light, the light source 122 is preferably a heater coil, which in this embodiment is preferably located in base 112. In this case, there is a risk of thermal injury from excessive exposure to heat or infrared energy. In order to reduce exposure of the tissue to IR energy, interposed between the light source 122 and the digit 114 is a electromechanical shutter 152. The shutter 152 is opened for a brief period, e.g. 1/60 second, allowing infrared light to be passed through the digit 114 and detected by the photodetector 130, which in this embodiment is located in the arm 116. Simultaneously, any other operating light source (e.g. an LED producing visible or very near infrared light) is turned off.

Measurements of absorbance of visible or infrared light at one or more specific wavelengths are made across a digit 14, earlobe, or other vascularized tissue at each of two points in the cardiac cycle, near peak systole and near nadir diastole. Simultaneously, the linear distance change due to the influx of arterial blood into the finger 14, or other tissue ($l_{pulse}$) is measured/computed as the difference between distance at the same two points in the cardiac cycle, e.g. peak systole ($l_{syst}$) and nadir diastole ($l_{diast}$).

$$l_{pulse} = l_{syst} - l_{diast}. \tag{1}$$

The absorbance difference at each wavelength $A_{pulse}$ is equal to the systolic—diastolic differences in total tissue absorbance:

$$A_{pulse} = A_{syst} - A_{diast}. \tag{2}$$

Total absorbance of the transilluminating light ($A_{total}$), either at systole or diastole, is the sum of three components: the absorbance by non-blood tissues of the finger ($A_{tissue}$), the absorbance by blood present at diastole (called "venous blood" for convenience) ($A_{ven}$), and absorbance by arterial blood infusing into the finger during systole ($A_{pulse}$):

$$A_{tot} = A_{tissue} + A_{ven} + A_{pulse}. \tag{3}$$

The sum of $A_{tissue}$ and $A_{ven}$ is virtually constant during systole and diastole, so $A_{pulse}$ is the absorbance change due to arterial blood infusing into the finger.

$A_{pulse}$ at any particular wavelength is also equal to the sum of the absorbances due to all of the substances present in the pulsatile arterial blood that absorb at that wavelength:

$$A_{pulse} = A_x + A_y + A_z + \ldots$$

Four configurations of the invention are described, depending upon the strength of the absorption peak used to make the measurement and the presence or absence of interfering substances absorbing at the same wavelength as the substance of interest.

In each of the computations, the results of the calculation may be compared to a reference. References can be derived from a variety of sources, one example of which is a compilation of data from one or more subjects with known or determined levels of blood components.

EXAMPLE I

Strong Absorption Peak, Without Interfering Substances.

Figure 3:
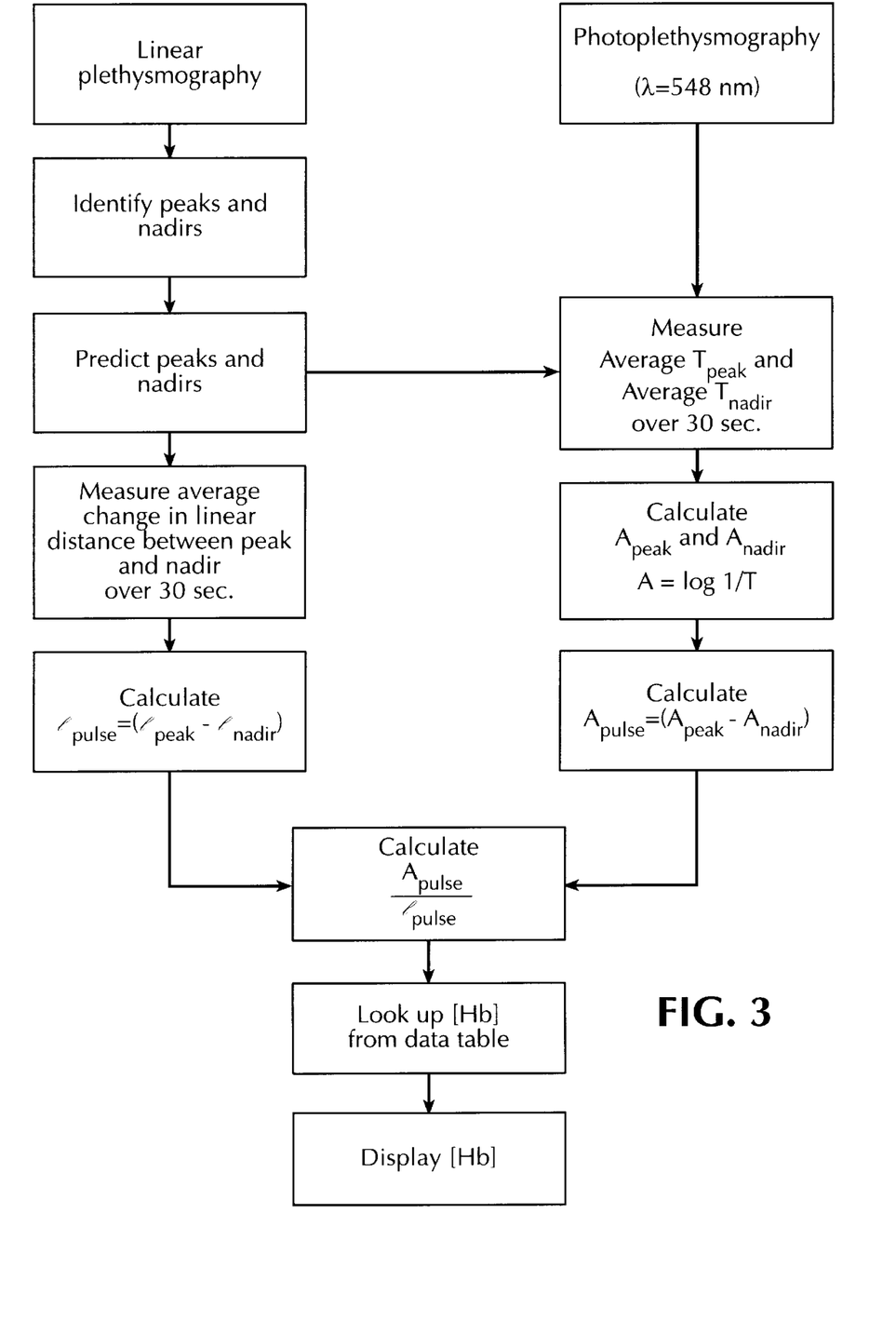
FIG. 3 is a flow chart delineating the steps of a sample method claimed for measuring blood component concentrations when the substance of interest absorbs very strongly at a particular wavelength relative to all other substances expected to be present in blood. (Example I)

As shown in FIG. 3, this configuration is used when the substance of interest absorbs very strongly at a particular wavelength relative to all other substances expected to be present in blood, as, for example, with hemoglobin (Hb) at a wavelength of 548 nm (0.548 μm), an isobestic point for oxy-, carboxy-, and reduced hemoglobins. (See, Siek T J, Rieders F., Determination of Carboxyhemoglobin in the Presence of Other Blood Hemoglobin Pigments By Visible Spectrophotometry, *J Forensic Sci* 29:39–54, 1984.) First, two points for analysis are determined, optimally peak systole and nadir diastole. For example, after approximately ten peaks and nadirs of the linear plethysmogram have been identified by the microprocessor, the mean durations between sequential peaks and nadirs are calculated and the times of occurrence of the next peak (systole) and nadir (diastole) are thereby predicted and selected for analysis during subsequent pulses. Since( absorbance at 0.548 μm is proportional to hemoglobin concentration and light pulse length, we can say:

$$A_{pulse.548} = [Hb] \cdot \epsilon_{Hb.548} \cdot l_{pulse} \quad (4)$$

where $\epsilon_{Hb.548}$ is the absorptivity of hemoglobin at 548 nm and $l_{pulse}$ is that portion of the light path length that is occupied by pulsatile arterial blood. Rearranging terms, $$[Hb] = A_{pulse.548} / (\epsilon_{Hb.548} \cdot l_{pulse}) \quad (5)$$

To calibrate the instrument, known concentrations of the substance of interest measured from conventional tests on drawn blood from a number of subjects with widely varying test results would be correlated with the ratio of $(A_{pulse.548}/l_{pulse})$, using linear or nonlinear regression analysis, with or without data transformation, as required. Alternatively, if no single regression formula accurately predicts [Hb] from the A/l ratio data over the entire range of A/l values, then separate regressions would be performed over various ranges cf A/l data. Subsequently, to use the instrument noninvasively, the derived regression formula or formulae would be used to calculate the concentration of the substance of interest.

Thus, the ratio of systolic-diastolic absorbance divided by the systolic—diastolic difference in length can be calibrated to measure hemoglobin concentration, virtually independent of the type and amount of tissue present.

Alternatively, the average rates of change (first derivatives with respect to time) of distance and light absorbance during periods of time that coincide with the steep phases of the linear- and photo-plethysmograms could be used in place of $l_{pulse}$ and $A_{pulse}$.

For practical purposes, since there is no currently available LED emitting at 548 nm, an alternative LED could be used, one emitting at e.g. 586 nm (e.g. the yellow LED made by Hewlett-Packard, part # HSMYR661/R761), a wavelength that is isobestic for oxy- and reduced hemoglobins, but is absorbed to a much lesser degree by carboxyhemoglobin and met-hemoglobin. It would provide reasonably accurate estimates of total hemoglobin concentrations in all subjects except those rare patients with very high carboxyhemoglobin (or met-hemoglobin) levels, and it would provide accurate estimates of acute changes in hemoglobin (e.g. hemorrhage), even in such patients.

Another alternative is that the proposed hemoglobin analyzer could be combined with standard, currently available pulse oximetry technology, using two wavelengths, 660 nm and 940 nm, to measure oxygen saturation, as well as hemoglobin, allowing arterial oxygen content (hemoglobin concentration (gm/dl) times fractional oxygen saturation times 1.34 ml/gm) to be determined. As with currently available pulse oximeters, the device would overestimate arterial oxygen saturation, and therefore arterial oxygen content, in subjects with high levels of carboxyhemoglobin. For that reason, improved estimates of arterial oxygen content would result if very narrow wavelength bands centered around 548 nm and 578 nm were used; both are isobestic for carboxy- and reduced hemoglobins, but 548 nm is isobestic for all three major species of hemoglobin, while 578 nm absorbs oxyhemoglobin more strongly than either carboxy- or reduced hemoglobin. Thus, the 548 nm wavelength would be used to measure total hemoglobin and the comparison of absorbance at 578 nm with that at 548 nm would allow calculation of oxyhemoglobin. Addition of a third wavelength (e.g. 597 nm, isobestic for oxy- and carboxy-hemoglobins, but absorbing reduced hemoglobin more strongly), would allow separate calculation of reduced and carboxy- in addition to oxy-hemoglobin levels. Similarly, light sources emitting at wavelengths of 506, 521, or 569 nm, all isobestic for reduced and oxyhemoglobins, could be used in place of the 548 nm emitter.

Those skilled in the art will recognize that many different sets of wavelengths would be suitable—if two wavelengths are used, oxy- and reduced hemoglobins could be discriminated; if three wavelengths are used, oxy-, carboxy-, and reduced hemoglobins could be discriminated; if four wavelengths are used, oxy-, carboxy-, met-, and reduced hemoglobins could be discriminated; and if five wavelengths are used, oxy-, carboxy-, met-, sulf-, and reduced hemoglobins could be discriminated.

EXAMPLE II

Weak Absorption Peak, without Interfering Substances.

This configuration would be used when only a weak absorption peak at a particular wavelength $\lambda_1$, exists for the substance of interest. In such cases, a second (reference) wavelength $(\lambda_2)$ with relatively low absorption by the substance of interest and by all other substances expected to be present in blood would also be studied. An example is glucose, which has a relatively weak absorption peak at 9.6 μm (9600 nm), but one that is specific to glucose, as compared to hemoglobin and plasma proteins. Zeller H, Novak P, Landgraf R., Blood Glucose Measurement by Infrared Spectroscopy, *Int J Artif Org* 12:12–35, 1989. The difference between absorbance at 9.6 μm and absorbance at a reference wavelength of 8.4 μm (8400 nm) would allow relatively good separation of glucose from plasma proteins and hemoglobin. The calculation is set forth in FIG. 4. In this case, since the total absorbance difference between the two wavelengths will be relatively independent of the concentration of substances other than glucose, $$A_{pulse\ 9.6} - A_{pulse\ 8.4} = (([glu] \cdot l_{pulse}) \cdot (\epsilon_{glu9.6} - \epsilon_{glu8.4})) + k. \quad (6)$$

Figure 4:
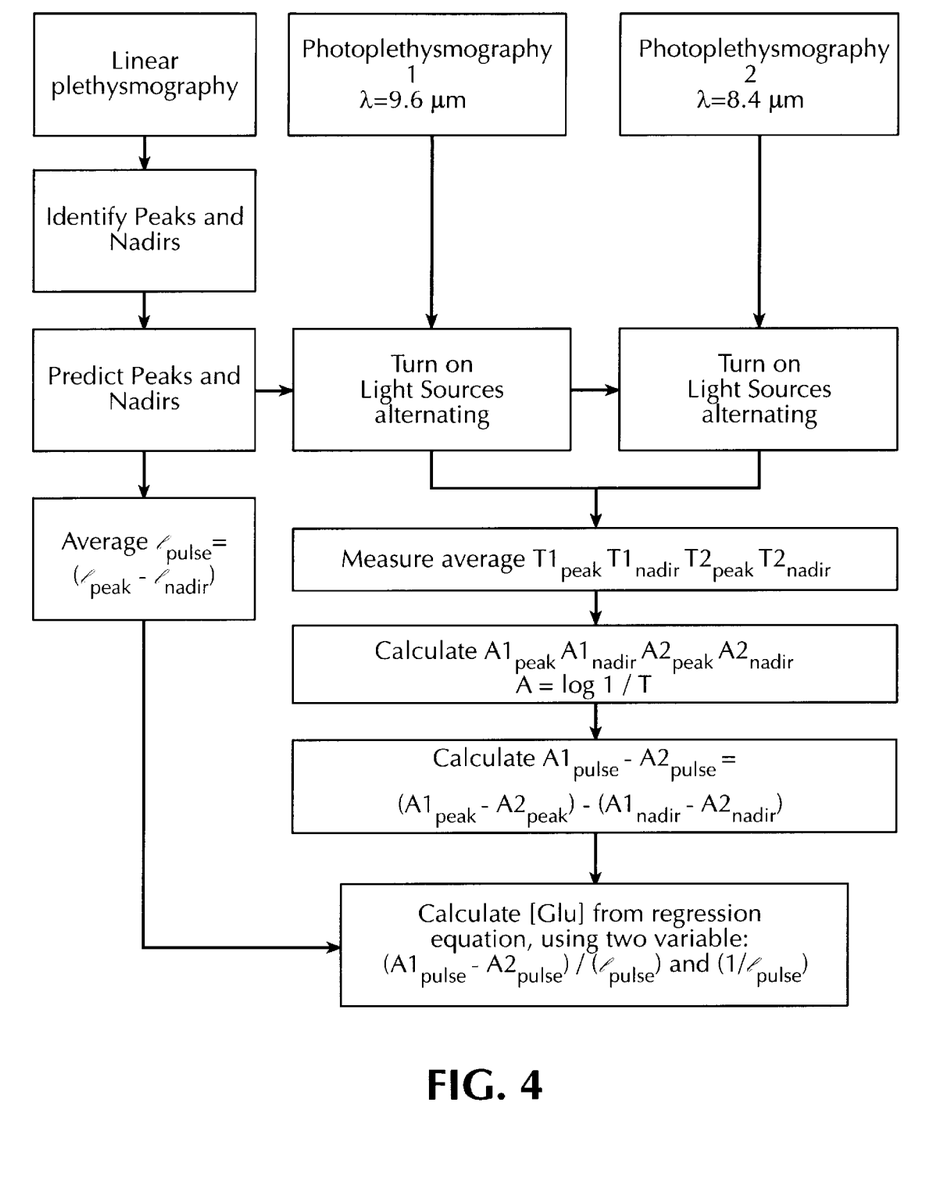
FIG. 4 is a flow chart delineating the steps of a sample method claimed for measuring blood component concentrations when there is only a weak absorption peak for the substance of interest, i.e., in the case of the measurement of glucose concentration. (Example II)

(where $\epsilon_{glu9.6}$ and $\epsilon_{glu8.4}$ are abscrptivities of glucose at 9.6 and 8.4 μm, respectively, and k is a small and, for practical purposes, constant term due to differences in absorbance of water and other blood components between 9.6 and 8.4 μm). Rearranging terms, $$[glu] = (A_{pulse\ 9.6} - A_{pulse\ 8.4} - k)/(l_{pulse} \cdot (\epsilon_{glu9.6} - \epsilon_{glu8.4})). \quad (7)$$

If we express $$A_{pulse9.6-8.4} = A_{pulse9.6} - A_{pulse8.4},$$

$$k_1 = 1/(\epsilon_{glu9.6} - \epsilon_{glu8.4}),$$

and $$k_2 = k/(\epsilon_{glu9.6} - \epsilon_{glu8.4}),$$

then $$[glu] = (k_1 \cdot A_{pulse9.6-8.4}/l_{pulse}) - (k_2/l_{pulse}). \quad (8)$$

The absorbances are calculated from measured transmittances, $l_{pulse}$ is measured, and $k_1$ and $k_2$ are constants that can be empirically determined by comparison with standard measurements.

To calibrate the instrument, known concentrations of the substance of interest measured from conventional tests on drawn blood would be correlated with two variables: $(A_{pulse9.6-8.4}/l_{pulse})$ and $(1/l_{pulse})$, using multiple regression analysis, with or without data transformation, as required. Alternatively, if no single regression formula accurately predicts [Glu] over the entire range of absorbance and length values, then separate regressions would be performed over various ranges of 1/l or absorbance data. Subsequently, to use the instrument noninvasively, the derived regression formula or formulae would be used to calculate the concentration of the substance of interest.

Optimally, the light sources would be switched on and off quickly enough so that the absorbance measurements at systole and diastole occur at essentially the same times for both wavelength. Alternatively, if the unavoidable differences in timing of absorbance measurements result in significant errors in prediction of the concentration of the substance of interest, then light path length data would be separately collected at the appropriate times to be related to each wavelength (e.g. $l_{pulse9.6}$ and $l_{pulse8.4}$) and the regression analysis would be carried out using three variables: $(A_{pulse\,9.6}/l_{pulse\,9.6}) - (A_{pulse\,8.4}/l_{pulse\,8.4})$, $1/l_{pulse\,9.6}$, and $1/l_{pulse\,8.4}$

EXAMPLE III

Interfering Substances Present

Figure 5:
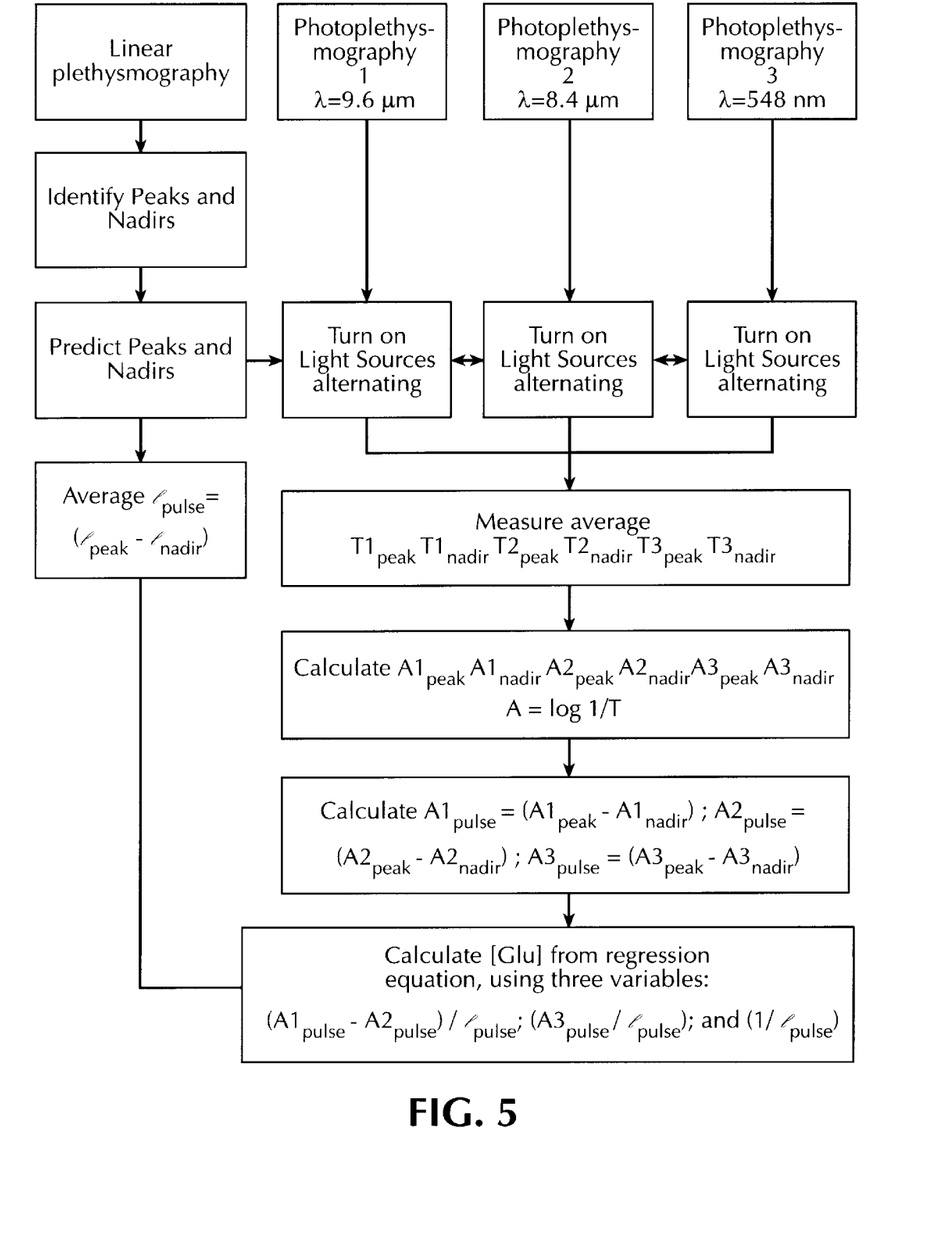
FIG. 5 is a flow chart delineating the steps of a sample method claimed for measuring blood component concentrations when a single interfering substance is present at the optimal wavelength. (Example III)

When a single interfering substance is present at the optimal wavelength to detect a substance, a third wavelength is used to correct for the presence of the interfering substance. An example is glucose and hemoglobin at a wavelength of 9.02 μm, a stronger peak for glucose than is 9.6 μm but one at which hemoglobin also absorbs. This calculation is shown in FIG. 5.

$$A_{pulse9.02} - A_{pulse8.4} = \{([glu] \cdot l_{pulse}) \cdot (\epsilon_{glu9.02} - \epsilon_{glu8.4})\} + \{([Hb] \cdot l_{pulse}) \cdot (\epsilon_{Hb9.02} - \epsilon_{Hb8.4})\} + k \quad (9)$$

But, as noted above, $[Hb] = A_{pulse.548}/(\epsilon_{Hb.548} \cdot l_{pulse})$. Substituting for [Hb]:

$$A_{pulse9.02} - A_{pulse8.4} = \{([glu] \cdot l_{pulse}) \cdot (\epsilon_{glu9.02} - \epsilon_{glu8.4})\} + \{(A_{pulse.548}/\epsilon_{Hb.548}) \cdot (\epsilon_{Hb9.02} - \epsilon_{Hb8.4})\} + k \quad (10)$$

Rearranging terms, $$[glu] = \{A_{pulse9.02} - A_{pulse8.4} - k - \{(A_{pulse\,0.548}/\epsilon_{Hb.548}) \cdot (\epsilon_{Hb9.02} - \epsilon_{Hb8.4})\}\} / \{(l_{pulse} \cdot (\epsilon_{glu9.02} - \epsilon_{glu8.4})\}. \quad (11)$$

All of the absorptivities are constants. If we express $A_{pulse9.02-8.4} = (A_{pulse9.02} - A_{pulse8.4})$, $k_1 = 1/(\epsilon_{glu9.02} - \epsilon_{glu8.4})$, $k_2 = (\epsilon_{Hb9.02} - \epsilon_{Hb8.4})/\{\epsilon_{Hb0.548} \cdot (\epsilon_{glu9.02} - \epsilon_{glu8.4})\}$, and $k_3 = k (\epsilon_{glu9.02} - \epsilon_{glu8.4})$, then $$[Glu] = (k_1 \cdot A_{pulse\,9.02-8.4}/l_{pulse}) - (k_2 \cdot A_{pulse.548}/l_{pulse}) - (k_3/l_{pulse}) \quad (12)$$

To calibrate the instrument, known concentrations of the substance of interest measured from conventional tests on drawn blood would be correlated with three variables: $(A_{pulse9.02-8.4}/l_{pulse})$, $(A_{pulse.548}/l_{pulse})$ and $(1/l_{pulse})$, using multiple regression analysis, with or without data transformation, as required. Alternatively, if no single regression formula accurately predicts [Glu] over the entire range of absorbance or length values, then separate regressions would be performed over various ranges of absorbance or length data. Subsequently, to use the instrument noninvasively, the derived regression formula or formulae would be used to calculate the concentration of the substance of interest.

Thus, for this configuration, physical measurements such as linear distance changes and absorbance changes at each of three different wavelengths, in this example, 0.548, 8.4, and 9.02 μm, would have to be studied. Those skilled in the art will recognize that many other sets of wavelengths could be used. Furthermore, the use of first derivative spectroscopy would improve the accuracy of the technique.

As in example II, it might be necessary to measure $l_{pulse}$ separately for each of the three wavelengths, making the calculations slightly more complex, as outlined above.

EXAMPLE IV

Interfering Substance at Strong Absorption Peak

Figure 6:
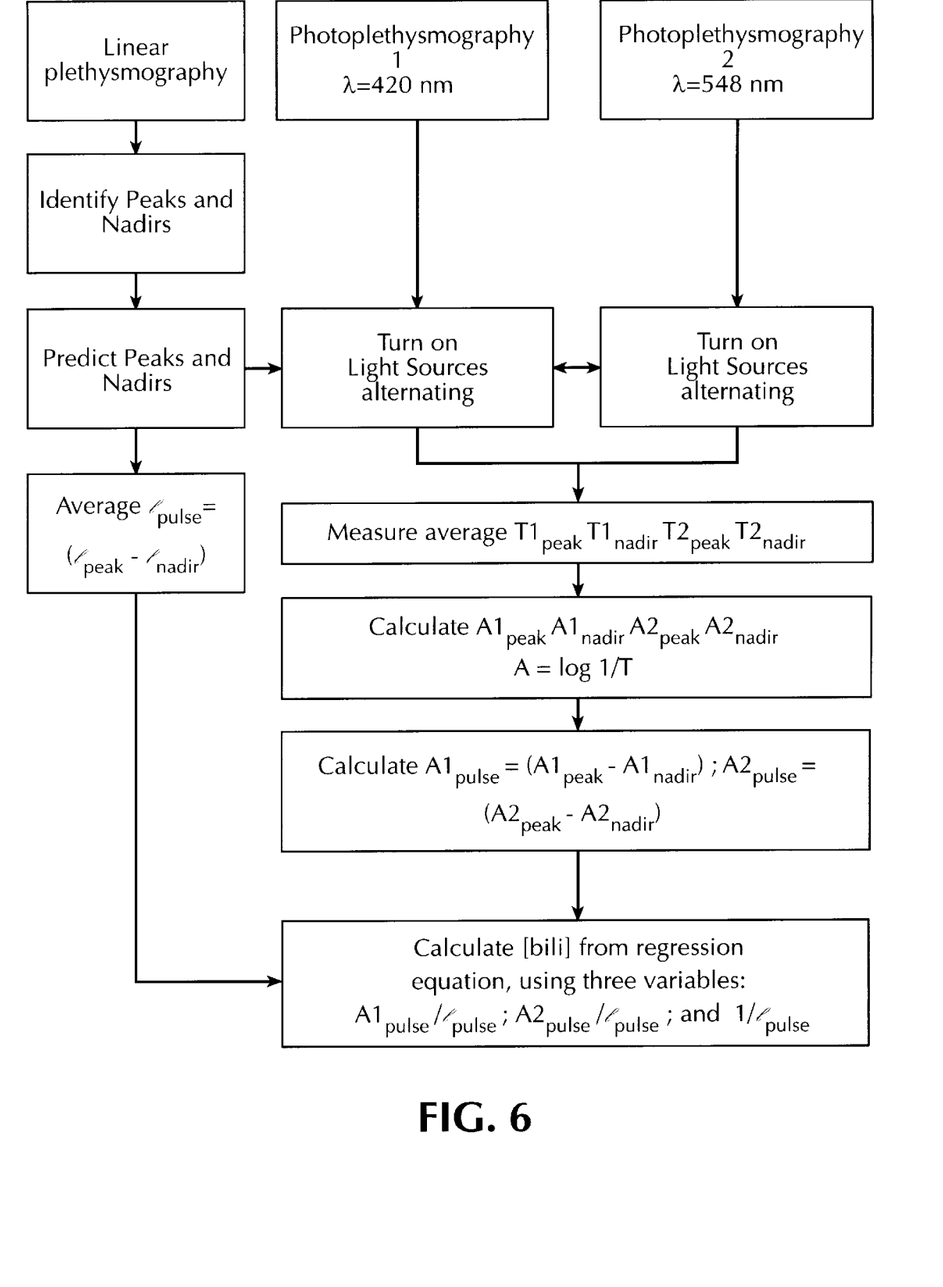
FIG. 6 is a flow chart delineating the steps of a sample method claimed for measuring blood component concentrations when a single interfering substance is present at the optimal wavelength, but no reference wavelength is needed, such as in the case of the measurement of bilirubin concentration. (Example IV)

Another example of a substance that could be measured after correction for the presence of an interfering substance is bilirubin. Bilirubin has a strong absorption peak around 420 nm, but hemoglobin absorbs substantially at that wavelength. As described above, bilirubin could be measured using two wavelengths: approximately 420 nm to detect bilirubin (without the need for a reference wavelength) and 548 nm (or 506, 521, 569, or 586 nm as discussed above) to correct for the presence of hemoglobin.

$$A_{pulse.42} = ([bili] \cdot l_{pulse} \cdot \epsilon_{b.42}) + ([Hb] \cdot l_{pulse} \cdot \epsilon_{Hb.42}) + k. \quad (13)$$

But, as noted above, $[Hb] = A_{pulse.548}/(l_{pulse} \cdot \epsilon_{b.548})$. Substituting for [Hb], $$A_{pulse.42} = ([bili] \cdot l_{pulse} \cdot \epsilon_{b.42}) + (A_{pulse.548} \cdot \epsilon_{Hb0.42}/\epsilon_{Hb.548}) + k. \quad (14)$$

Rearranging terms, $$[bili] = \{A_{pulse.42} - (A_{pulse.548} \cdot \epsilon_{b.42}/\epsilon_{Hb.548}) - k\}/l_{pulse} \cdot \epsilon_{b.42}). \quad (15)$$

If we express $k_1 = 1/\epsilon_{b.42}$, $k_2 = \epsilon_{Hb.42}/(\epsilon_{Hb.548} \cdot \epsilon_{b.42})$, and $k_3 = k/\epsilon_{b.42}$, then $$[bili] = (k_1 \cdot A_{pulse.42}/l_{pulse}) - (k_2 \cdot A_{pulse.548}/l_{pulse}) - (k_3/l_{pulse}). \quad (16)$$

To calibrate the instrument, known concentrations of the substance of interest measured from conventional tests on drawn blood would be correlated with three variables: $A_{pulse.42}/l_{pulse}$, $A_{pulse.548}/l_{pulse}$ and $1/l_{pulse}$, using multiple regression analysis, with or without data transformation, as required. Alternatively, if no single regression formula accurately predicts the substance of interest over the entire range of absorbance and length values, then separate regressions would be performed over various ranges of 1/l or absorbance data. Subsequently, to use the instrument noninvasively, the derived regression formula or formulae would be used to calculate the concentration of the substance of interest.

Again, as in examples II and III, it might be necessary to measure $l_{pulse}$ separately for each of the wavelengths.

For each of the above configurations, the concentration of the appropriate blood component is calculated from one of the regression equations derived as described above. Data are averaged over the period of time required to generate reliable average data, e.g. over every thirty to sixty seconds, or every 50 to 100 pulses.

Although an exemplary embodiment of the invention has been described in detail above, those skilled in the art will readily appreciate that many additional modifications are possible in the exemplary embodiment without materially departing from the novel teachings and advantages of the invention. Accordingly, all such modifications are intended to be included within the scope of the invention as defined in the following claims.

What is claimed is:

1. A non-invasive method for measuring the concentration of a blood component in a subject's blood, said method comprising the steps of:
    (a) providing at least one light source for directing light of at least one wavelength through a tissue of the subject in which light absorbance of arterial blood can be detected by measuring changes in absorbance during pulsatile flow of blood,
    (b) providing at least one detector for detecting the portion of the light not absorbed by the tissue of the subject;
    (c) measuring the absorbance of the light at the wavelength by the tissue at both the systolic and diastolic phase of the pulsatile flow;
    (d) determining the physical dimension of said tissue at both the systolic and diastolic phase of the pulsatile flow;
    (e) calculating a ratio of the change in light absorbance between the systolic and diastolic phase divided by the change in the physical dimension of said tissue between the systolic and diastolic phase;
    (f) determining the concentration of the blood component by comparing the ratio calculated in step (e) to a reference.

2. The method of claim 1, wherein the light source emits light at a wavelength wherein the blood component absorbs strongly relative to all other substances expected to be present in the subject's blood.

3. The method of claim 1, wherein the blood component is hemoglobin and the wavelength of light is approximately 548 nm.

4. The method of claim 1, wherein the blood component is hemoglobin and the wavelength of light is approximately 506 nm.

5. The method of claim 1, wherein the blood component is hemoglobin and the wavelength of light is approximately 521 nm.

6. The method of claim 1, wherein the blood component is hemoglobin and the wavelength of light is approximately 569 nm.

7. The method of claim 1, wherein the blood component is hemoglobin and the wavelength of light is approximately 586 nm.

8. The method of claim 1 wherein the light source is a light-emitting diode, a laser, a heater coil, or an incandescent lamp.

9. The method of claim 1 wherein the detector is a photodetector.

10. The method of claim 1, which the physical dimension of said tissue is the linear distance between the light source and the detector.

11. The method of claim 10 wherein the linear distance between the light source and the detector is measured using a linear displacement transducer, a pair of opposing piezo-electric crystals or a magnetometer.

12. The method of claim 1 wherein the reference is the ratio of the change in light absorbance between the systolic and diastolic phase divided by the change in physical dimension between the systolic and diastolic phase for subjects with known concentrations of the blood component.

13. A non-invasive method for measuring the concentration of a blood component in a subject's blood, said method comprising the steps of:
    (a) choosing a first wavelength of light at which the blood component absorbs light relatively strongly and all other substances expected to be present in the subject's blood absorb light to a lesser degree;
    (b) choosing a second wavelength of light to be used as a reference wavelength, said reference wavelength absorbed at a relatively low level by both the blood component of inte(rest and all other substances expected to be present in the subject's blood;
    (c) providing a first light source for directing light at the first wavelength through a tissue of the subject in which light absorbance of arterial blood can be detected by measuring changes in absorbance during pulsatile flow of blood;
    (d) providing a second light source for directing light at the reference wavelength through the tissue of the subject, the second light source either being the first light source adapted to emit light at more than one wavelength or a separate light source located adjacent to the first light source;
    (e) providing at least one detector for detecting the portion of the light of the first wavelength and the light of the reference wavelength not absorbed by the tissue of the subject;
    (f) determining a physical dimension of the tissue at both the systolic and diastolic phases of the subject's pulsatile flow;
    (g) calculating the change in the physical dimension of said tissue between the systolic and diastolic phases of the subject's pulsatile flow;
    (h) measuring the absorbance of light at the first wavelength and the reference wavelength at the systolic and diastolic phases of pulsatile blood flow;
    (i) calculating the change in light absorbance between the systolic and diastolic phases for both the first wavelength and reference wavelength;
    (j) calculating the difference between the changes in absorbances at each of the two wavelengths calculated in step (i);
    (k) calculating a value by applying a formula dividing the difference between the changes in absorbances at the two wavelengths as calculated in step (i) by the change in the physical dimension of said tissue between the systolic and diastolic phases as calculated in step (g);
    (l) determining the concentration of the blood component by comparing the value calculated n step (k) to a reference.

14. The method of claim 13 wherein step (k) comprises calculating the value by applying an empirically derived regression equation employing two variables, the first variable being the ratio of the difference between the changes in absorbances at the two wavelengths as calculated in step (j) to the change in the physical dimension of said tissue between the systolic and diastolic phases as calculated in step (g) and the second variable being the reciprocal of the change in the physical dimension of said tissue between the systolic and diastolic phases as calculated in step (g).

15. The method of claim 13 wherein said blood component is glucose.

16. The method of claim 15 wherein said first wavelength is approximately 9600 nm.

17. The method of claim 15 wherein said reference wavelength is approximately 8400 nm.

18. The method of claim 13 wherein at least one of said light sources is a heater coil.

19. The method of claim 18 wherein said first and second light sources are the same heater coil and band pass filters are interposed between the heater coil and the tissue.

20. The method of claim 13 wherein at least one of said light sources is a light-emitting diode, laser or incandescent lamp.

21. The method of claim 13 wherein the physical dimension of said tissue is the linear distance between the light sources and the detector.

22. The non-invasive method of claim 21 wherein the linear distance between the light sources and the detector is measured using a linear displacement transducer, a pair of opposing piezoelectric crystals or a magnetometer.

23. The method of claim 13 wherein the reference is a value calculated in accordance with step (k) for reference subjects with known concentrations of the blood component.

24. A non-invasive method for measuring the concentration of a blood component in a subject's blood by light absorbance when an interfering substance absorbs at the optimal wavelength for detecting the concentration of the blood component, said method comprising:

(a) choosing three wavelengths of light, a first wavelength at which both the blood components and the interfering substance absorb relatively strongly in comparison to all other substances expected to be present in the subject's blood, a second wavelength at which the blood component and the interfering substance absorb differentially, and a third wavelength at which the blood component and the interfering substance absorb at approximately the same low level;

(b) providing a first light source for directing light at the first wavelength through a tissue of the subject in which light absorbance of arterial blood can be detected by measuring changes in absorbance during pulsatile flow of blood;

(c) providing a second light source for directing light at the second wavelength through said tissue of the subject, the second light source either being the first light source adapted to emit light at more than one wavelength or a separate light source located adjacent the first light source, (d) providing a third light source for directing light at the third wavelength through the tissue or the subject, the third light source being either the first or second light sources adapted to emit light at more than one wavelength or a separate light source located adjacent the first and second light sources;

(e) providing at least one detector for detecting the portion of the light of the first, second and third wavelengths not absorbed by the tissue of the subject;

(f) measuring the absorbance of light at each of the three wavelengths at the systolic and diastolic phase of pulsatile blood flow;

(g) calculating the change in light absorbance between the systolic and diastolic phases for each of the first, second, and third wavelengths;

(h) calculating the difference between the changes in absorbances between the systolic and diastolic phases between the first and second wavelengths;

(i) determining a physical dimension of said tissue at both the systolic and diastolic phases of the subject's pulsatile flow;

(j) calculating the change in the physical dimension of said tissue between the systolic and diastolic phases of the subject's pulsatile flow;

(k) calculating a value by applying a formula employing three empirically derived regression constants and three variables, the first variable being the ratio of the difference between the changes in absorbances between the systolic and diastolic phases at the first two wavelengths as calculated in step (h) to the change in the physical dimension of said tissue between the systolic and diastolic phases as calculated in step (j), the second variable being the ratio of the change in light absorbance between the diastolic and systolic phases for the third wavelength as calculated in step (g) to the change in the physical dimension of said tissue as calculated in step (j), and the third variable being the reciprocal of the change in the physical dimension of said tissue as calculated in step (j);

(l) determining the concentration of said blood component by comparing the value calculated in step (k) to a reference.

25. The method of claim 24 wherein said blood component is glucose.

26. The method of claim 25 wherein said interfering substance is hemoglobin.

27. The method of claim 25 wherein said first wavelength is approximately 9020 nm.

28. The method of claim 25 wherein said second wavelength is approximately 8400 nm.

29. The method of claim 24 wherein said third wavelength is approximately 548 nm.

30. The method of claim 24 wherein at least one of said light sources is a heater coil.

31. The method of claim 30 wherein said light sources are the same heater coil and band pass filters are interposed between the heater coil and the tissue.

32. The method of claim 24 wherein at least one of said light sources is a light emitting diode, a laser or an incandescent lamp.

33. The method of claim 24 wherein the detector is a photodetector.

34. The method of claim 24 wherein the physical dimension of said tissue is the linear distance between the light sources and the detector.

35. The non-invasive method of claim 34 wherein the linear distance between the light sources and the detector is measured using a linear displacement transducer, a pair of opposing piezoelectric crystals or a magnetometer.

36. The method of claim 24 wherein the reference is a value calculated in accordance with step (k) for reference subjects with known concentrations of the blood component.

37. A non-invasive method for measuring the concentration of a blood component in a subject's blood when an interfering substance absorbs at the optimal wavelength for detecting the concentration of the blood component, said method comprising:

(a) choosing a first wavelength of light at which the blood component absorbs light relatively strongly in comparison to all other substances expected to be present in the subject's blood and the interfering substance also absorbs light to a substantial degree;

(b) choosing a second wavelength of light at which the interfering substance absorbs light to a substantial degree;

(c) providing a first light source for directing light at the first wavelength through tissue of the subject in which the light absorbance of arterial blood can be detected by measuring changes in absorbance during pulsatile flow of blood;

(d) providing a second light source for directing light at the second wavelength through the tissue of the subject, the second light source either being the first light source adapted to emit light at more than one wavelength or a separate light source located adjacent to the first light source;

(e) providing at least one detector for detecting the portion of the light of the first wavelength and the second wavelength not absorbed by the tissue of the subject;

(f) determining a physical dimension of said tissue at both the systolic and diastolic phases of the subject's pulsatile flow;

(g) calculating the change in the physical dimension of said tissue between the systolic and diastolic phases of the subject's pulsatile flow;

(h) measuring the absorbance of light for each of the first wavelength and the second wavelength at the systolic and diastolic phases of pulsatile blood flow;

(i) calculating the change in light absorbance between the systolic and diastolic phases for both the first wavelength and second wavelengths;

(j) calculating a ratio of the change in light absorbance as calculated in step (i) to the change in the physical dimension of said tissue and the detector as calculated in step (g) for each of the first and second wavelengths;

(k) calculating a value by applying a formula employing three empirically derived regression constants and three variables, the first variable being the ratio of the change in light absorbance at the first wavelength to the change in the physical dimension of the tissue between the systolic and diastolic phases as determined in step (j), the second variable being the ratio of the change in light absorbance at the second wavelength to the change in the physical dimension of said tissue between systolic and diastolic phases as determined in step (j) and the third variable being the reciprocal of the change in the physical dimension of said tissue between the systolic and diastolic phases as calculated in step (g); and (l) determining the concentration of the blood component by comparing the value calculated in step (k) to a reference.

38. The method of claim 37 wherein said reference is a value calculated in accordance with step (k) for reference subjects with known concentrations of the blood component.

39. The method of claim 37 wherein said blood component is bilirubin.

40. The method of claim 39 wherein said interfering substance is hemoglobin.

41. The method of claim 39 wherein said first wavelength is approximately 420 nm.

42. The method of claim 39 wherein said second wavelength is approximately 548 nm.

43. The method of claim 37 wherein the physical dimension of said tissue is the linear distance between the light sources and the detector.

44. The method of claim 43 wherein the linear distance between the light sources and the detector is measured using a linear displacement transducer, a pair of opposing piezoelectric crystals or a magnetometer.

45. A device for the non-invasive measurement of the concentration of a blood component in a subject's blood, said device comprising:

(a) at least one light transmission set comprising:
  (i) at least one light source;
  (ii) at least one detector for detecting the light emitted by the light source mounted apart from the light source such that the subject's tissue is adapted to be interposed between the detector and light source, the light source mounted so as to transilluminate the tissue and the detector mounted so as to detect the light from said light source not absorbed by said tissue, (b) a base adapted for holding a portion of the tissue of the subject through which pulsatile flow of arterial blood can be detected, said base including at least a portion of the light transmission set;

(c) means for measuring changes in a physical dimension of said tissue between the light source and the detector;

(d) means for transmitting data from the light detector;

(e) means for transmitting data from the means for measuring change in said physical dimension of said tissue; and (f) means for receiving the transmitted data and for calculating the concentration of the blood component by calculating the ratio of change in light absorbance in the systolic and diastolic phase divided by the change in physical dimension of the tissue and comparing the ratio to a reference.

46. The device of claim 45 wherein said light source is a light-emitting diode, a laser, a heater coil or an incandescent lamp.

47. The device of claim 45 wherein the detector is a photodetector.

48. The device of claim 45 wherein the physical dimension of said tissue is the linear distance between the light source and the detector.

49. The device of claim 48 wherein said means for measuring changes in linear distance is a linear displacement transducer, a pair of opposing piezoelectric crystals or a magnetometer.

50. The device of claim 45 wherein the reference is a ratio of change in light absorbance in the systolic and diastolic phases divided by the change in the physical dimension of said tissue calculated for reference subjects with known concentrations of the blood component.

* * * * *